(12) United States Patent
Cumming

(10) Patent No.: US 9,295,546 B2
(45) Date of Patent: Mar. 29, 2016

(54) ANTERIOR CAPSULE DEFLECTOR RIDGE

(71) Applicant: James Stuart Cumming, Laguna Beach, CA (US)

(72) Inventor: James Stuart Cumming, Laguna Beach, CA (US)

( * ) Notice: Subject to any disclaimer, the term of this patent is extended or adjusted under 35 U.S.C. 154(b) by 91 days.

(21) Appl. No.: 14/035,813

(22) Filed: Sep. 24, 2013

(65) Prior Publication Data

US 2015/0088254 A1 Mar. 26, 2015

(51) Int. Cl.
*A61F 2/16* (2006.01)

(52) U.S. Cl.
CPC .............. *A61F 2/1635* (2013.01); *A61F 2/1629* (2013.01); *A61F 2002/1689* (2013.01); *A61F 2220/0091* (2013.01); *A61F 2250/0036* (2013.01)

(58) Field of Classification Search
CPC ........... A61F 2/14; A61F 2/16; A61F 2/1613; A61F 2/1616; A61F 2/1618; A61F 2/1624; A61F 2/1629; A61F 2/1635; A61F 2002/1681; A61F 2002/1689
See application file for complete search history.

(56) References Cited

U.S. PATENT DOCUMENTS

| | | | |
|---|---|---|---|
| 2,834,023 A | 5/1958 | Lieb | |
| 4,073,014 A | 2/1978 | Poler | |
| 4,118,808 A | 10/1978 | Poler | |
| 4,122,556 A | 10/1978 | Poler | |
| 4,159,546 A | 7/1979 | Shearing | |
| 4,168,547 A | 9/1979 | Konstantinov et al. | |
| 4,173,798 A | 11/1979 | Welsh | |
| 4,174,543 A | 11/1979 | Kelman | |
| 4,206,518 A | 6/1980 | Jardon et al. | |
| 4,244,060 A | 1/1981 | Hoffer | |
| 4,254,509 A | 3/1981 | Tennant | |
| 4,277,851 A | 7/1981 | Choyce | |
| 4,298,995 A | 11/1981 | Poler | |
| 4,304,012 A | 12/1981 | Richard | |
| 4,409,690 A | 10/1983 | Gess | |
| 4,409,691 A | 10/1983 | Levy | |
| 4,424,597 A | 1/1984 | Schlegel | |
| 4,441,217 A | 4/1984 | Cozean, Jr. | |
| 4,477,931 A | 10/1984 | Kelman | |
| 4,573,998 A | 3/1986 | Mazzocco | |
| 4,585,457 A | 4/1986 | Kalb | |
| 4,605,411 A | 8/1986 | Fedorov et al. | |
| 4,629,462 A | 12/1986 | Feaster | |
| 4,648,878 A | 3/1987 | Kelman | |
| 4,664,665 A | 5/1987 | Reuss et al. | |
| 4,664,666 A | 5/1987 | Barrett | |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — Andrew Iwamaye
*Assistant Examiner* — Leslie Lopez
(74) *Attorney, Agent, or Firm* — Knobbe Martens Olson & Bear LLP

(57) ABSTRACT

An intraocular lens designed to separate and prevent fibrosis of the anterior capsular rim with the posterior capsule where it surrounds the optic.

12 Claims, 1 Drawing Sheet

(56) References Cited

U.S. PATENT DOCUMENTS

| | | |
|---|---|---|
| 4,673,406 A | 6/1987 | Schlegel |
| 4,681,102 A | 7/1987 | Bartell |
| 4,704,123 A | 11/1987 | Smith |
| 4,710,195 A | 12/1987 | Giovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,139,518 A | 8/1992 | White |
| 5,141,507 A | 8/1992 | Parekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore et al. |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |

(56) References Cited

U.S. PATENT DOCUMENTS

| | | | |
|---|---|---|---|
| 7,229,475 B2 | 6/2007 | Glazier | |
| 7,229,476 B2 | 6/2007 | Azar | |
| 7,300,464 B2 | 11/2007 | Tran | |
| 7,326,246 B2 | 2/2008 | Brady | |
| 7,341,599 B1 | 3/2008 | Peyman | |
| 7,435,258 B2 | 10/2008 | Blake | |
| 7,435,259 B2 | 10/2008 | Cumming | |
| 7,553,327 B2 | 6/2009 | Cumming | |
| 7,662,180 B2 | 2/2010 | Paul et al. | |
| 7,763,070 B2 | 7/2010 | Cumming | |
| 7,837,730 B2 | 11/2010 | Cumming | |
| 7,981,155 B2 | 7/2011 | Cumming | |
| 7,985,253 B2 | 7/2011 | Cumming | |
| 8,038,711 B2 | 10/2011 | Clarke | |
| 8,080,056 B2 | 12/2011 | Cumming | |
| 8,100,965 B2 | 1/2012 | Cumming et al. | |
| 8,109,998 B2 | 2/2012 | Cumming | |
| 8,163,015 B2 | 4/2012 | Cumming | |
| 8,216,308 B2 | 7/2012 | Blake et al. | |
| 8,388,608 B1 | 3/2013 | Kaluzna | |
| 8,523,942 B2 | 9/2013 | Cumming | |
| 8,734,512 B2 | 5/2014 | Cumming | |
| 8,764,823 B2 | 7/2014 | Cumming | |
| 9,034,036 B2 | 5/2015 | Cumming | |
| 2001/0001836 A1 | 5/2001 | Cumming | |
| 2002/0120329 A1 | 8/2002 | Lang et al. | |
| 2002/0138140 A1* | 9/2002 | Hanna | 623/6.37 |
| 2003/0060881 A1 | 3/2003 | Glick et al. | |
| 2003/0078658 A1 | 4/2003 | Zadno-Azizi | |
| 2003/0097177 A1 | 5/2003 | Tran | |
| 2003/0109925 A1 | 6/2003 | Ghazizadeh et al. | |
| 2003/0135272 A1 | 7/2003 | Brady et al. | |
| 2003/0142269 A1 | 7/2003 | Cumming | |
| 2003/0171808 A1 | 9/2003 | Phillips | |
| 2003/0171809 A1 | 9/2003 | Phillips | |
| 2003/0187505 A1 | 10/2003 | Liao | |
| 2003/0199977 A1 | 10/2003 | Cumming | |
| 2003/0204257 A1 | 10/2003 | Southard | |
| 2004/0002757 A1 | 1/2004 | Lai et al. | |
| 2004/0015236 A1 | 1/2004 | Sarfarazi | |
| 2004/0082993 A1 | 4/2004 | Woods | |
| 2004/0082994 A1 | 4/2004 | Woods et al. | |
| 2004/0111152 A1 | 6/2004 | Kelman | |
| 2004/0148023 A1 | 7/2004 | Shu | |
| 2004/0215207 A1 | 10/2004 | Cumming | |
| 2004/0220666 A1 | 11/2004 | Cumming | |
| 2004/0243232 A1 | 12/2004 | Cumming | |
| 2004/0249456 A1 | 12/2004 | Cumming | |
| 2005/0021140 A1 | 1/2005 | Liao | |
| 2005/0027354 A1 | 2/2005 | Brady et al. | |
| 2005/0075732 A1* | 4/2005 | Israel | 623/6.43 |
| 2005/0096741 A1 | 5/2005 | Cumming | |
| 2005/0107875 A1 | 5/2005 | Cumming | |
| 2005/0125058 A1 | 6/2005 | Cumming et al. | |
| 2005/0137703 A1 | 6/2005 | Chen | |
| 2005/0267576 A1 | 12/2005 | Cumming | |
| 2005/0288784 A1 | 12/2005 | Peyman | |
| 2006/0064077 A1 | 3/2006 | Peyman | |
| 2006/0064162 A1 | 3/2006 | Klima | |
| 2006/0100704 A1 | 5/2006 | Blake et al. | |
| 2006/0111776 A1 | 5/2006 | Glick et al. | |
| 2006/0116764 A1 | 6/2006 | Simpson | |
| 2006/0149369 A1 | 7/2006 | Cumming et al. | |
| 2007/0032867 A1 | 2/2007 | Cumming | |
| 2007/0129800 A1 | 6/2007 | Cumming | |
| 2007/0129803 A1 | 6/2007 | Cumming et al. | |
| 2007/0135915 A1 | 6/2007 | Klima | |
| 2007/0142908 A1 | 6/2007 | Xu | |
| 2007/0198084 A1 | 8/2007 | Cumming et al. | |
| 2007/0244472 A1 | 10/2007 | Kuhn et al. | |
| 2008/0027538 A1 | 1/2008 | Cumming | |
| 2008/0027539 A1 | 1/2008 | Cumming | |
| 2008/0027540 A1 | 1/2008 | Cumming | |
| 2008/0046077 A1 | 2/2008 | Cumming | |
| 2008/0086208 A1 | 4/2008 | Nordan | |
| 2008/0154362 A1 | 6/2008 | Cumming | |
| 2008/0154363 A1* | 6/2008 | Cumming | A61F 2/1613 623/6.37 |
| 2008/0281415 A1 | 11/2008 | Cumming | |
| 2008/0281416 A1 | 11/2008 | Cumming | |
| 2008/0288066 A1 | 11/2008 | Cumming | |
| 2008/0294254 A1 | 11/2008 | Cumming et al. | |
| 2008/0319545 A1 | 12/2008 | Cumming | |
| 2009/0005866 A1 | 1/2009 | Cumming | |
| 2009/0234449 A1 | 9/2009 | De Juan, Jr. et al. | |
| 2009/0248154 A1 | 10/2009 | Dell | |
| 2010/0004742 A1 | 1/2010 | Cumming | |
| 2010/0057202 A1 | 3/2010 | Bogaert | |
| 2011/0313519 A1 | 12/2011 | Cumming | |
| 2011/0313524 A1 | 12/2011 | Cumming | |
| 2011/0313525 A1 | 12/2011 | Cumming | |
| 2012/0296424 A1 | 11/2012 | Betser | |
| 2013/0073039 A1 | 3/2013 | Mirlay | |
| 2013/0231742 A1 | 9/2013 | Deacon et al. | |
| 2014/0088699 A1 | 3/2014 | Cumming | |
| 2014/0094909 A1 | 4/2014 | Cumming | |
| 2014/0155871 A1 | 6/2014 | Cumming | |
| 2015/0012088 A1 | 1/2015 | Cumming | |
| 2015/0073550 A1 | 3/2015 | Cumming | |
| 2015/0182327 A1 | 7/2015 | Cumming | |
| 2015/0182328 A1 | 7/2015 | Cumming | |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |

OTHER PUBLICATIONS

Final Office Action for U.S. Appl. No. 13/017,189 dated Jul. 18, 2014 in 10 pages.
Final Office Action for U.S. Appl. No. 13/017,189 dated Jan. 13, 2015 in 20 pages.
Final Office Action for U.S. Appl. No. 13/092,359 dated Mar. 5, 2013 in 11 pages.
Final Office Action for U.S. Appl. No. 13/092,359 dated Feb. 6, 2015 in 21 pages.
Final Office Action for U.S. Appl. No. 13/111,599 dated May 2, 2013 in 10 pages.
Final Office Action for U.S. Appl. No. 13/111,599 dated Feb. 6, 2015 in 21 pages.
Final Office Action for U.S. Appl. No. 13/155,327 dated Dec. 10, 2012 in 10 pages.
Final Office Action for U.S. Appl. No. 13/953,605 dated Sep. 25, 2014 in 17 pages.
Final Office Action for U.S. Appl. No. 14/274,352 dated Jun. 8, 2015 in 27 pages.
Final Office Action for U.S. Appl. No. 13/891,088 dated Jul. 2, 2015 in 17 pages.
Final Office Action for U.S. Appl. No. 14/143,612 dated Mar. 20, 2015 in 14 pages.
Final Office Action for U.S. Appl. No. 14/257,933 dated Mar. 19, 2015 in 23 pages.
International Search Report and Written Opinion for PCT/US13/61452 dated Feb. 24, 2014 in 11 pages.
International Search Report and Written Opinion for PCT/US2014/057037 dated Jan. 20, 2015 in 12 pages.

(56) References Cited

OTHER PUBLICATIONS

Office Action for U.S. Appl. No. 13/017,189 dated May 9, 2013 in 9 pages.
Office Action for U.S. Appl. No. 13/092,359 dated Oct. 25, 2012 in 10 pages.
Office Action for U.S. Appl. No. 13/092,359 dated Sep. 8, 2014 in 15 pages.
Office Action for U.S. Appl. No. 13/092,359 dated Jun. 5, 2015 in 11 pages.
Office Action for U.S. Appl. No. 13/111,599 dated Jan. 2, 2013 in 11 pages.
Office Action for U.S. Appl. No. 13/111,599 dated Sep. 5, 2014 in 13 pages.
Office Action for U.S. Appl. No. 13/111,599 dated Jun. 26, 2015 in 12 pages.
Office Action for U.S. Appl. No. 13/155,327 dated Jul. 20, 2012 in 7 pages.
Office Action for U.S. Appl. No. 13/155,327 dated Apr. 26, 2013 in 7 pages.
Office Action for U.S. Appl. No. 14/270,166 dated Mar. 3, 2015 in 19 pages.
Office Action for U.S. Appl. No. 13/953,605 dated May 20, 2014 in 9 pages.
Office Action for U.S. Appl. No. 14/274,352 dated Feb. 12, 2015 in 10 pages.
Office Action for U.S. Appl. No. 13/891,088 dated Aug. 13, 2014 in 25 pages.
Office Action for U.S. Appl. No. 13/910,076 dated Nov. 7, 2014 in 12 pages.
Office Action for U.S. Appl. No. 13/910,076 dated Apr. 10, 2015 in 26 pages.
Office Action for U.S. Appl. No. 14/035,821 dated Apr. 13, 2015 in 33 pages.
Office Action for U.S. Appl. No. 14/257,933 dated Oct. 31, 2014 in 9 pages.
Response to Office Action for U.S. Appl. No. 13/017,189 dated Aug. 8, 2013 in 5 pages.
Response to Final Office Action for U.S. Appl. No. 13/017,189 dated Dec. 18, 2014 in 10 pages.
Response to Office Action for U.S. Appl. No. 13/092,359 dated Jan. 31, 2013 in 8 pages.
Response to Final Office Action for U.S. Appl. No. 13/092,359 dated Jul. 29, 2013 in 7 pages.
Response to Final Office Action for U.S. Appl. No. 13/092,359 dated Jan. 8, 2015 in 9 pages.
Response to Final Office Action for U.S. Appl. No. 13/092,359 dated May 6, 2015 in 9 pages.
Response to Office Action for U.S. Appl. No. 13/111,599 dated Jul. 30, 2013 in 6 pages.
Response to Final Office Action for U.S. Appl. No. 13/111,599 dated Jan. 6, 2015 in 12 pages.
Response to Office Action for U.S. Appl. No. 13/111,599 dated Jun. 8, 2015 in 13 pages.
Response to Office Action for U.S. Appl. No. 13/155,327 dated Oct. 26, 2012 in 5 pages.
Response to Office Action for U.S. Appl. No. 13/155,327 dated Apr. 10, 2013 in 5 pages.
Response to Office Action for U.S. Appl. No. 13/155,327 dated Jul. 25, 2013 in 5 pages.
Response to Office Action for U.S. Appl. No. 13/953,605 dated Aug. 19, 2014 in 7 pages.
Response to Final Office Action for U.S. Appl. No. 13/953,605 dated Dec. 18, 2014 in 12 pages.
Response to Office Action for U.S. Appl. No. 14/274,352 dated May 12, 2015 in 10 pages.
Response to Office Action for U.S. Appl. No. 13/891,088 dated Dec. 15, 2014 in 8 pages.
Response to Office Action for U.S. Appl. No. 13/910,076 dated Feb. 9, 2015 in 10 pages.
Response to Office Action for U.S. Appl. No. 14/143,612 dated Jan. 5, 2015 in 8 pages.
Response to Office Action for U.S. Appl. No. 14/143,612 dated Jul. 17, 2015 in 8 pages.
Response to Office Action for U.S. Appl. No. 14/257,933 dated Feb. 2, 2015 in 10 pages.
First Action Interview Pre-Interview Communication for U.S. Appl. No. 14/741,230 dated Jul. 30, 2015 in 5 pages.
International Search Report and Written Opinion for PCT/US2014/072518 dated Jul. 23, 2015 in 15 pages.
Office Action for U.S. Appl. No. 14/712,827 dated Oct. 6, 2015 in 38 pages.
Office Action for U.S. Appl. No. 14/143,612 dated Jul. 27, 2015 in 13 pages.
Office Action for U.S. Appl. No. 14/257,933 dated Aug. 31, 2015 in 14 pages.
Response to Office Action for U.S. Appl. No. 13/910,076 dated Oct. 9, 2015 in 15 pages.
Response to Office Action for U.S. Appl. No. 14/035,821 dated Oct. 12, 2015 in 15 pages.
Final Office Action for U.S. Appl. No. 13/017,189 dated Oct. 28, 2015 in 9 pages.
Office Action for U.S. Appl. No. 14/584,188 dated Oct. 6, 2015 in 21 pages.
Preliminary Amendment for U.S. Appl. No. 14/741,230 dated Oct. 14, 2015 in 12 pages.
Response to Office Action for U.S. Appl. No. 13/092,359 filed Oct. 26, 2015 in 14 pages.
Response to Office Action for U.S. Appl. No. 14/274,352 filed Oct. 22, 2015 in 14 pages.
Response to Office Action for U.S. Appl. No. 13/910,076 filed Oct. 9, 2015 in 15 pages.
Response to Office Action for U.S. Appl. No. 14/035,821 filed Oct. 12, 2015 in 15 pages.

* cited by examiner

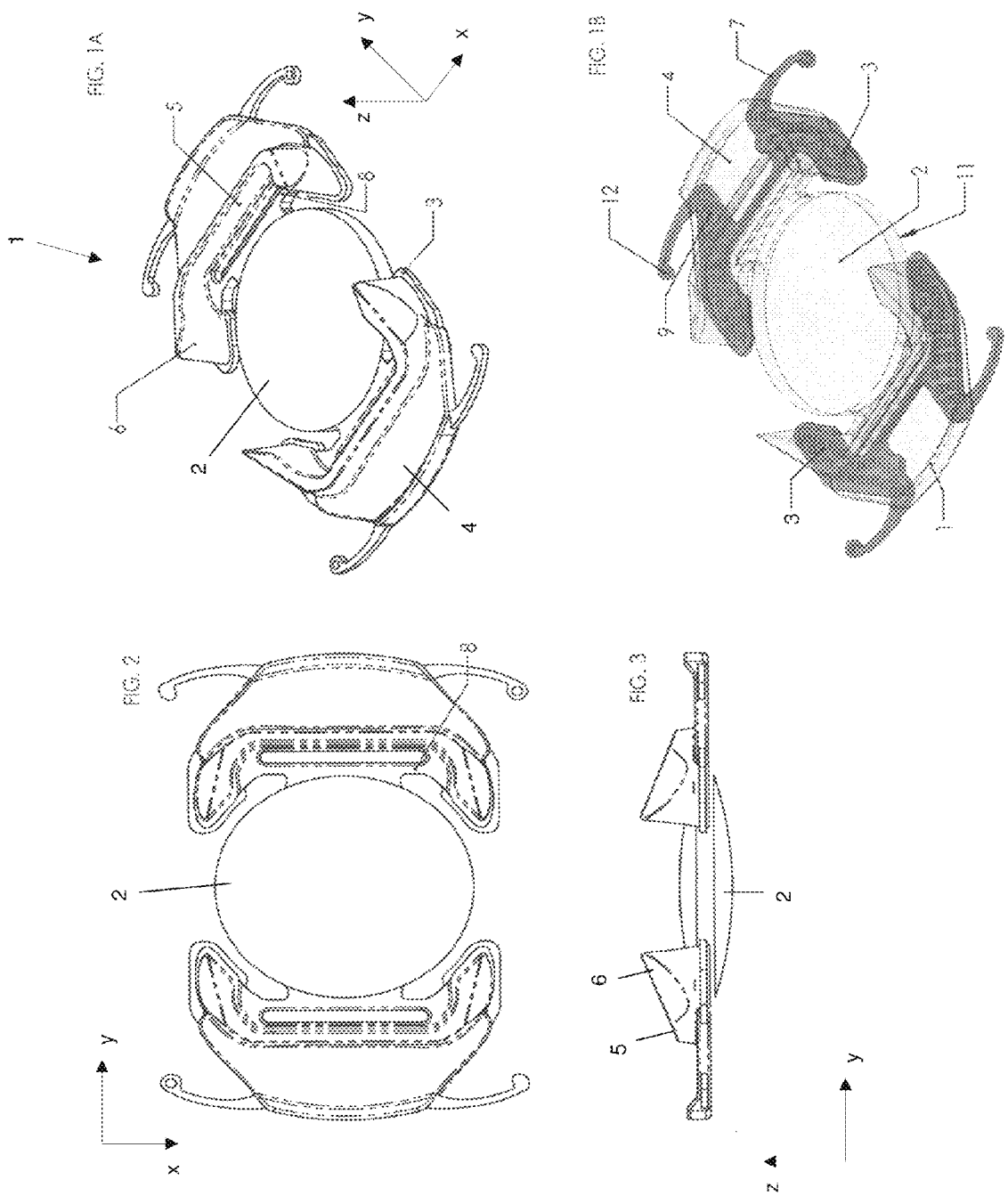

ANTERIOR CAPSULE DEFLECTOR RIDGE

RELATED APPLICATIONS

Various applications related to intraocular lenses are incorporated herein by reference in their entirety. These applications include the following: U.S. Publication No. 20110313519, filed Jan. 31, 2011; U.S. Publication No. 2011/0313524, filed Apr. 22, 2011; U.S. Publication No. 2011/0313525, filed May 19, 2011; U.S. Publication No. 2011/0313526, filed Jun. 7, 2011; U.S. Pat. No. 8,523,942, filed May 15, 2012; U.S. Publication No. 2012/0310344, filed May 16, 2012; U.S. application Ser. No. 13/891,088, filed May 9, 2013; and U.S. application Ser. No. 13/910,076, filed Jun. 4, 2013.

BACKGROUND

1. Field

The present disclosure relates to lenses.

2. Description of the Related Art

There have been several intraocular lens models designed to allow patients to see at all distances following lens extraction. The most commonly used of these are the multifocal lenses, where the optic in the intraocular lens has two or three focal lengths. These lenses have problems since they require the patient to visually select the lens component's focal length appropriate to the target in their sight.

Since the lenses have multiple focal lengths, only a fraction of the light is available at the focal length being observed. This results in loss of contrast sensitivity.

The multiple focal lengths also cause dysphotopsias, especially at night when glare and halos are present. This has led to many multifocal lenses being explanted.

Accommodating lenses have also been developed. Constriction of the ciliary muscle during accommodation causes an increase in pressure in the posterior, the vitreous cavity of the eye, and a reduction of the pressure in the anterior chamber of the eye. These pressure changes have been utilized to cause the optic of a flexible intraocular lens to move forwards and backwards in response to the pressure changes. This allows the patient to see seamlessly at all distances. Such designs, however, can be improved.

SUMMARY

Certain aspects of this disclosure are directed toward a flexible accommodating intraocular lens having plate haptics connected to an optic by connection members. The plate haptics can include one or more anterior ridge protrusions positioned on the plate haptics, for example, extending across a width of the plate haptics. The one or more anterior ridge protrusions can be designed to separate the optic of the lens from the anterior capsule of the human lens capsular bag, into which the lens has been implanted. In certain aspects, the plate haptics can be longitudinally rigid.

Certain aspects of this disclosure are directed toward a flexible accommodating intraocular lens having plate haptics connected to an optic by connection members. The intraocular lens can also include paddles. One or more anterior ridge protrusions can be positioned on the paddles, for example, the protrusions can extend across the paddles. The one or more anterior ridge protrusions can be designed to separate the optic of the lens from the anterior capsule of the human lens capsular bag, into which the lens has been implanted.

Certain aspects of this disclosure are directed toward a flexible accommodating intraocular lens having plate haptics connected to an optic by connection members. The intraocular lens can also include paddles. One or more anterior ridge protrusions can be positioned on the plate haptics and the paddles. The one or more anterior ridge protrusions can be designed to separate the optic of the lens from the anterior capsule of the human lens capsular bag, into which the lens has been implanted.

Certain aspects of this disclosure are directed toward a flexible accommodating intraocular lens having plate haptics connected to an optic by connection members. The intraocular lens can include one or more anterior ridge protrusions positioned adjacent to the connection members. The one or more anterior ridge protrusions can be configured to separate the optic of the intraocular lens from the anterior capsule of the human lens capsular bag into which the lens is implanted.

Certain aspects of this disclosure are directed toward a flexible accommodating intraocular lens having plate haptics connected to an optic by connection members. The intraocular lens can include one or more anterior ridge protrusions configured to separate the optic of the intraocular lens from the anterior capsule of the human lens capsular bag into which the lens is implanted.

In any of the above-mentioned aspects, the intraocular lens can further include lateral paddle-like extensions. In certain aspects, the plate haptic and lateral paddle-like extensions can have anterior ridge protrusions configured to separate the anterior capsule from the optic of the lens and its connections to the optic. In certain aspects, the anterior protrusions can incline anteriorly between about 5° and 30°, for example, about 15°, 20°, or 25°.

In any of the above-mentioned aspects, the anterior ridge protrusions can extend across most of the proximal width of the plate haptic.

In any of the above mentioned aspects, the anterior protrusions can extend fully across the plate haptics.

In any of the above-mentioned aspects, the connection between the plate haptic and optic can be a flexible stretchable connecting bar or torsion bar.

In any of the above-mentioned aspects, the connection between the plate haptic and optic can be a hinge.

In any of the above mentioned aspects, the protrusions can provide a space to allow the optic and its connections to the plate haptics to move forward relative to both the proximal and distal ends of the plate haptics.

In any of the above mentioned aspects, the connection members can be stretchable.

In any of the above mentioned aspects, the one or more anterior ridge protrusions can extend transversely across the width of the plate haptics.

In any of the above mentioned aspects, the one or more anterior ridge protrusions can be positioned adjacent to the connection members.

In any of the above mentioned aspects, the one or more anterior protrusions can surround the optic by more than 180° of a circumference of the optic In any of the above mentioned aspects, the one or more anterior ridge protrusions can extend along an end of the haptic closest to the optic.

In any of the above mentioned aspects, the haptics can include one or more anterior ridge protrusions.

In any of the above mentioned aspects, the paddles can include one or more anterior ridge protrusions.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 1 A & B are a perspective view of various embodiments of an intraocular lens.

FIG. 2 is a front elevational view.

FIG. 3 is a side elevational view.

DETAILED DESCRIPTION

For an accommodating lens which functions by moving an optic along the axis of the eye by repeated flexions, flexible materials can be used to form the optic. Silicone is a useful material, since silicone is stretchable and flexible and can be bent or stretched probably several million times without showing any damage. A torsion bar, connecting bar, groove or hinge can be placed across the plate haptic adjacent to the optic, as part of the lens design to facilitate movement of the optic relative to the outer ends of the haptics. (Another material for the lenses is acrylic, although acrylic can fracture if repeatedly flexed.)

Unfortunately it has proven to be difficult to show movement of the lens optic, despite many attempts having been made using chemicals in conjunction with "A" (acoustic) scans to stimulate and relax the ciliary muscle.

These methods attempting to demonstrate movement have resulted in conflicting results. Some of the studies demonstrate a small forward movement and others a backward movement or no movement at all.

Additionally, although the distance and intermediate vision with the currently available accommodating lenses have been excellent, the near vision sometimes requires low power reading glasses to read comfortably.

What is useful, are that the designs provide movement of the optic with accommodation. Preferably, such designs provide for favorable vision at far distance, intermediate distance as well as near. Various accommodating lenses are described in: U.S. Publication No. 20110313519, filed Jan. 31, 2011; U.S. Publication No. 2011/0313524, filed Apr. 22, 2011; U.S. Publication No. 2011/0313525, filed May 19, 2011; U.S. Publication No. 2011/0313526, filed Jun. 7, 2011; U.S. Pat. No. 8,523,942, filed May 15, 2012; U.S. Publication No. 2012/0310344, filed May 16, 2012; U.S. application Ser. No. 13/891,088, filed May 9, 2013; and U.S. application Ser. No. 13/910,076, filed Jun. 4, 2013, all of which are hereby incorporated by reference in their entirety and features of such lenses may be included in various embodiments described herein.

To insert an artificial lens, the natural lens is initially removed. During this lens extraction, a circular hole is torn in the front of the lens capsule, and the center nucleus and peripheral cortex take out. Subsequently the intraocular lens is inserted into the empty capsular bag, which is attached to the circular ciliary muscle.

Healing (fibrosis) then commences. The anterior capsular rim fibroses to the posterior capsule commencing at the periphery or cul de sac of the capsular bag, to cover the peripheral lens structure to fixate and center the lens in place within the bag.

The accommodating lenses have generally flat uniplanar plate haptic designs. Plate lenses are manufactured as uniplanar devices; however, the length of the lens from the ends of the two plate haptics (10.5 mm) is slightly longer than the diameter of the capsular bag (10.0 mm). This causes the lens to be vaulted backwards when placed into the capsular bag.

Upon accommodation with constriction of the circular ciliary muscle its diameter is reduced, the posteriorly vaulted plate haptic lens is then compressed end-to-end.

In some of the accommodating lens designs the plate haptics and optic have been designed to swing forward with the increasing posterior cavity (vitreous cavity) pressure overcoming the end-to-end pressure, which would tend to move the optic posteriorly.

In this accommodating lens design, the connection between the optic and the plate haptics is configured to stretch like an elastic band upon end-to-end compression of the plate haptics, with a concomitant increase in vitreous cavity pressure causing the optic to move forward.

For this mechanism of action to be successful, space in front of the optic and the component connecting the plate haptic to the optic is desirable, in order to allow forward movement of the optic.

Since the hole torn by the surgeon, in the front of the capsular bag is usually 5.0 mm in diameter and the lens optic is also 5.0 mm in diameter, fibrosis of the anterior and posterior components of the capsular bag shrink-wraps the lens to cover the connecting components of the plate haptic to the optic. This prevents or limits the forward movement of the whole lens and the optic.

Various embodiments of the invention described herein provide a space in front of the optic and its connections to the plate haptics such that it has room to move forward by stretching of these connections during accommodation, with its concomitant increase in pressure in the posterior chamber (vitreous cavity) of the eye.

According to various embodiments of the invention, an accommodating lens comprises a lens with a flexible solid optic attached to which are two or more extended portions, which may be plate haptics, capable of multiple flexes and stretches at their junction with the optic. The lens has fixation and centration features at the distal ends of the plate haptics. There may be a hinge, torsion bar, connecting bar, or groove connecting the plate haptic to the optic. The connection may facilitate the anterior and posterior movement of the optic relative to both the proximal and distal ends of the extended portions, in response to pressure changes in the vitreous (posterior) and anterior chamber cavities within the eye.

Various embodiments include a modification of a plate haptic designed with lateral rigid paddles, which along with the proximal end of the plate haptics partially surround the optic through more than 180° of its circumference. These modifications provide a space in front of the optic and its connections to its plate haptics to enable the optic to move forward into the space. Various embodiments of the accommodating intraocular lens may thereby allow the patient to focus automatically and to see seamlessly from distance to near with accommodation.

Moreover, a space is provided by adding one or more elevated ridges to the front surface of the plate haptics close to the optic, and/or the rigid paddles that partially surround the optic. The ridges on both plate haptics and/or paddles may together partially extend about the optic across more than 180° of the optics circumference. (The ridge need not be contiguous on each plate haptic but can be provided by two or more spaced apart ridges.) The ridge (or ridges) prevents fusion of the anterior and posterior capsule portions across the elastic stretchable connections between the optic and plate haptics to provide a space in front of the optic and its connections to the plate haptics, thereby allowing it to move forward with accommodation.

In certain aspects, there is only one ridge disposed along each plate haptic or paddle. The ridge may be disposed along an edge of the haptic closest to the optic. The ridge may extend across less than about 10% of the haptic, across at least about 10% and/or less than or equal to about 20%, across at least about 20% and/or less than or equal to about 30%, across at least about 30% and/or less than or equal to about 40%, across at least about 40% and/or less than or equal to about 50%, across at least about 50% and/or less than or equal to about 60%, across at least about 60% and/or less than or equal to about 70%, across at least about 70% and/or less than or equal to about 80%, across at least about 80% and/or less than or equal to about 90%, or across at least about 90% and/or less than or equal to about 100% of a width of the haptic. In other aspects, two, three, four, or more ridges are disposed along each plate haptic and/or paddle. The multiple number of ridges may be evenly or unevenly spaced apart across a width of the haptic. The ridges on both plate haptic may together surround the optic by more than 180 degrees or less than 180 degrees. For example, the ridges together may surround less than or equal to about 30 degrees, at least about 30 degrees and/or less than or equal to about 60 degrees, at least about 45 degrees and less than or equal to about 75 degrees, at least about 60 degrees and/or less than or equal to about 90 degrees, at least about 75 degrees and less than or equal to about 105 degrees, at least about 90 degrees and/or less than or equal to about 120 degrees, at least about 105 degrees and/or less than or equal to about 135 degrees, at least about 120 degrees and/or less than or equal to about 150 degrees, at least about 135 degrees and/or less than or equal to about 165 degrees, at least about 150 degrees and/or less than or equal to about 180 degrees of the optic. In certain aspects, a plurality of ridges are disposed along the haptic and/or paddle, each ridge extending across, less than or equal to about 10%, less than or equal to about 5%, less than or equal to about 2%, or less than or equal to about 1% of a width of the haptic. In certain aspects, a plurality of ridges are disposed along the haptic and/or paddle, each ridge extending across, at least about 10%, at least about 5%, at least about 2%, or at least about 1% of a width of the haptic. Ranges within any of these values are also possible.

Thus, various embodiments of the present invention are directed to an accommodating lens with an anterior elevated, anterior capsule support ridge, protrusion, or projection, deflecting the anterior capsule portion away from the optic and its connections to the plate haptic.

Accordingly, various embodiment of the present invention include features that can provide an improved form of an accommodating lens.

In various embodiments, the optic is of a foldable, flexible silicone, acrylic or hydrogel material and the haptic plates are of a foldable material, e.g., silicone, that will withstand multiple foldings without damage. The distal ends of the plate haptics may have flexible T-shaped fixation/centration devices and are contiguous with a chassis designed to make the plates rigid longitudinally but flexible transversely and molded into the plate haptics. The longitudinally rigid chassis may be contiguous with the rigid paddles.

FIGS. 1-3 illustrate in detail an embodiment comprising an intraocular lens 1 comprising a flexible solid optic 2, preferably although not necessarily made of silicone, and portions extending therefrom, plate haptic, 4, which may be longitudinally rigid and which are capable of transverse flexes without damage and formed, for example, of silicone and polyimide. In some embodiments, the optic 2, and haptic 4, are of one piece, and are uniplanar. Additionally, the one or more haptics 4, are flat on their posterior surface extend distally from opposite sides of the optic 2.

According to various embodiments of the present disclosure, the lens plate haptics can have lateral paddle-like extensions (or projections) 3 extending therefrom. In some embodiments, the proximal plate haptics and the paddles partially surround the optic by more than 180° of the circumference of the optic. The embodiments shown in FIGS. 1-3 includes an anterior bar-like protrusion (or projection) 5 across the part of the plate haptic 4 proximal to the optic 2, extending as a ridge along the width of the haptic and/or the rigid paddle-like lateral extensions 3 (see portions 6 of protrusions above paddle-like lateral extensions). The protrusion 5 may also turn to extend longitudinally (e.g., parallel to the y-axis) at the portion 6 thereof over the lateral paddle like extensions 3. The anterior bar-like protrusion 5 may increase in height as it progresses from a central location proximal to the optic laterally towards the lateral paddle-like extensions 3 and/or longitudinally toward the optic 2 and may incline anteriorly and proximally toward the optic 2 from 5° to 30° at the portions 6 above the lateral paddle-like extensions 3. The anterior bar-like protrusion 5 deflects the anterior portion of the capsule away from the stretchable connecting components 8 and the lens optic 2, to provide a space to allow the optic to move forward during accommodation. The lens 1 preferably comprises an accommodating intraocular lens. The optic diameter can range from approximately 3.5-8.0 mm and may be 4.5-5.0 mm. The length of the plates from tip to tip may be from 10.0 to 11.5 mm, preferably 10.5 mm, and from loop tip to loop tip from 10.0 to 14.0, preferably 11.5 mm.

The haptics 4 preferably are longitudinally rigid plate haptics having arcuate outer edges including loops 7. The loops 7 when unrestrained are somewhat less curved in configuration as shown in FIGS. 1 A & B and 2. The lens 1, including the optic 2, haptics 4, and torsion or connecting bar 8 are preferably formed of a flexible material such as silicone, acrylic, or hydrogel. The loops 7, chassis 9, and paddles can be of a material different from the haptics 4 and made of polyimide, prolene, or titanium. The loops 7, a chassis 9, and contiguous paddles 3 may be molded into the plate haptics, making the plate haptics 4 longitudinally rigid but flexible transversely. This enables the lens to be folded longitudinally so that it can be inserted into the eye through an incision of 3.0 mm or less. Torsion or connecting bars 8 form elastic stretchable connections between the haptics 4 and the optic 2 such that the optic when subjected to a posterior pressure can move forward at the optic/haptic connection by rotation and stretching of the torsion bars connection.

The junction of the posterior surface of the optic 2 to the side of the optic is a sharp edge or junction 11 designed to reduce the migration of cells across the posterior capsule portion of the lens post-operatively and thereby reduce the incidence of posterior capsular opacification and the necessity of YAG posterior capsulotomy.

FIGS. 1 A & B and 2 illustrates the haptics 4, loops 7, and the connector torsion bars 8 extending from the haptics to the optic 2. Hard knobs 12 can be provided on the ends of the loops 7 and are designed to fixate the loops 7 in the capsular bag of the eye.

The intraocular lenses can be implanted in the capsular bag of the eye after removal of the natural lens. The lenses are inserted into the eye through an incision of 3.0 mm or less from an insertion device folded longitudinally, and placed into the capsular bag through a generally circular opening torn by the surgeon into the anterior capsular portion of the human lens. The outer ends of the haptics, and the loops, are in close proximity with the bag cul-de-sac, and the loops 7 are deflected centrally to size and fixate the lens into the capsular bag. The lenses are implanted in the same manner as described above and as known in the art.

In various embodiments, the lens optic and plate material is silicone, and the chassis, loops and paddles are polyimide.

As discussed above, in various embodiments, one or more protrusions or projections 5, 6 can be provided to reduce the amount of fusion of the anterior and posterior capsule portions across the elastic stretchable connections between the optic 2 and plate haptics 4. Such a feature can provide a space in front of the optic 2 and its connections to the plate haptics 4, thereby allowing the optic to move forward with accommodation. The protrusions 5, 6 may have various shapes and sizes and may comprise ridges. Such elevated portions 5, 6 may reduce the incidence of problematic fusion of the anterior and posterior capsule portions, which inhibits motion of the optic that occurs with accommodation.

In various embodiments, the protrusions or ridges 5, 6 are longer than high or wide. The protrusions may be narrower at the top than at the base. In some embodiments, an apex or edge may be disposed at the top of the protrusion.

In the embodiment shown in FIGS. 1-3, for example, the protrusions 5, 6 extend most of the transverse dimension of the lens 1 (e.g., parallel to the x-axis). For example, the protrusion 5, 6 shown extends substantially the full width in the lateral direction (e.g., parallel to the x-axis) of the haptic 4 and the paddles 3. In the embodiment shown, the length of the protrusion 5, 6 is at least the diameter of the optic 2, although the protrusions can be shorter. In some embodiments, one or more of the protrusions or ridges 5, 6 such as shown in FIGS. 1-3 comprise multiple shorter segments or protrusions (e.g., 2, 3, 4, 5, 6, 7, 8, 9, 10, or more). Various embodiments can include one or more shorter segments or protrusions, which may be positioned near the connection members 8, positioned on the haptics, and/or positioned on the paddles. In some instances, the multiple shorter segments or protrusions may be arranged along the transverse dimension of the lens 1. In various embodiments, the shape of the protrusion 5 is linear or substantially linear. In the embodiments shown in FIGS. 1-3, the protrusion 5 is somewhat in the shape of a "C" with a substantial portion extending in the transverse direction (e.g., parallel to the x-axis) and portions 6 at the end extending in the orthogonal, longitudinal direction (e.g., parallel to the y-axis). Other shapes are possible. Additionally, as described above, instead of a single protrusion 5 on each side of the optic 2, multiple smaller protrusions or segments (e.g., 2, 3, 4, 5, 6, 7, 8, 9, 10, or more) may be used. These protrusions or segments may be separated by spaces. In certain embodiments, a single protrusion has multiple peaks.

In various embodiments, the protrusions or projections 5 extend about a large portion of the optic 2 to reduce the incidence of problematic fixation of the capsular bag which inhibits forward motion of the optic with accommodation. The protrusions 5 can be larger or smaller and extend over larger or smaller distances. For example, the protrusions 5 together can extend about at least 50%, 60%, 70%, or 80% of the perimeter (e.g., circumference) of the optic 2. In some embodiments, however, the protrusions 5 can extend about less than 100%, 90%, 80%, 70%, or 60% of the perimeter (e.g., circumference) of the optic 2 as well. Any combination of these values is possible as are values outside these ranges for some embodiments. Similarly, the protrusions 5 together can extend about at least 180°, 190°, 200°, 210°, 220°, 230°, 240°, 250°, 260°, 270°, 280°, 290°, 300°, 310°, 320°, 330°, 340°, or 350° of the optic 2. In some embodiments, however, the protrusions 5 can extend about less than 350°, 340°, 330°, 320°, 310°, 300°, 290°, 280°, 270°, 260°, 240°, 230°, 220°, or 210° of the optic 2. Any combination of these values is possible as are values outside these ranges for some embodiments. As illustrated in FIGS. 1-3, multiple protrusions 5 that are not contiguous together extend about a substantial portion of the optic 2 and accordingly, multiple protrusions can be used to provide the above referenced coverage. For example, two protrusions 5 each extending between about 30% to 40% of the perimeter (e.g. circumference) of the optic 2 may be used to cover between about 60% to 80% of the optic. As another example, two protrusions 5 each extending between 120° to 150° about the optic 2 may be used to cover between about 260° to 300° of the optic 2. Thus, the ranges above may be reduced in half for each of two protrusions, or reduced more if additional protrusions are employed. As discussed above, however, different size protrusions extending about larger or smaller portions of the optics 2 may be used and more than two protrusions may also be used.

In various embodiments the protrusions 5 are arranged on opposite sides of the optic 2 as illustrated in FIGS. 1-3. However, the arrangement may vary. Moreover, multiple protrusions 5, for example, 3, 4, 5, 6, 7, 8, 9, 10, or more, may be arranged to reduces the problematic fixation of the capsular bag on the optics 2 and connections with the haptic 4.

The height of the protrusions 5, 6 may be between 3%, 4%, 5%, 6%, and 11%, 12%, 13%, 15% of the longitudinal extent of the lens 1 (e.g., in direction parallel to y-axis). Similarly, the height of the protrusions may be between 6%, 8%, 10%, 12% to 20%, or 25% of the diameter of the optic 2. Larger or smaller heights are possible as well.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the lenses shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A flexible intraocular lens comprising:
   a pair of plate haptics, each plate haptic being connected to an optic, each plate haptic comprising:
      a proximal edge;
      a distal edge;
      opposing lateral edges extending from the proximal edge to the distal edge, the proximal edge being closer to the optic than the distal edge;
      a first lateral paddle portion; and
      a second lateral paddle portion, each paddle portion comprising a co-planar cantilevered extension of a respective plate haptic and extending proximally and around opposite sides of the optic, each of the first and second lateral paddle portions formed by a portion of a respective one of the lateral edges and a portion of a respective proximal edge, a proximal end of each of the first and second lateral paddle portions comprising a rounded convex end portion being spaced apart from the optic;
   a single chassis embedded in each plate haptic and extending at least from the respective proximal edge of said respective plate haptic to the distal edge of said respective plate haptic, the single chassis extending through the first and second lateral paddle portions of said respective plate haptic, the single chassis comprising a material more rigid than the plate haptics; and
   a single anterior ridge protrusion extending anteriorly from each plate haptic and anteriorly of the optic, the single anterior ridge protrusion being spaced apart from a respective distal edge of the respective plate haptic and extending across the respective proximal edge of the respective plate haptic, the single anterior ridge protrusion comprising:
      a first lateral ridge portion extending across the first lateral paddle portion of said respective plate haptic;
      a second lateral ridge portion extending across a width of said respective plate haptic; and
      a third lateral ridge portion extending across the second lateral paddle portion of said respective plate haptic;
      wherein the single anterior ridge protrusion is configured to separate the optic of the flexible intraocular lens from the anterior capsule of the human lens capsular bag when the flexible intraocular lens is implanted;
   wherein the pair of plate haptics, including each of the first and second lateral paddle portions, together partially surround the optic by more than 180 degrees;
   wherein the single anterior ridge protrusions together partially surround the optic by more than 180 degrees;
   wherein each plate haptic and its respective chassis and single anterior ridge protrusion form a C-shaped structure partially surrounding the optic; and
   wherein an outermost lateral periphery of the flexible intraocular lens is defined at least in part by a portion of a periphery of the optic and one of said opposing lateral edges of each plate haptic.

2. The flexible intraocular lens of claim 1, wherein each single anterior ridge protrusion inclines proximally toward the optic and anteriorly at an angle between five degrees and thirty degrees.

3. A flexible intraocular lens according to claim 2, wherein each single anterior ridge protrusion inclines anteriorly 15°.

4. A flexible intraocular lens according to claim 2, wherein each single anterior ridge protrusion inclines anteriorly 20°.

5. A flexible intraocular lens according to claim 2, wherein each single anterior ridge protrusion inclines anteriorly 25°.

6. A flexible intraocular lens according to claim 1, wherein each plate haptic is coupled to the optic by at least one stretchable connection member between each plate haptic comprising a flexible torsion bar configured to rotate or stretch when subjected to a posterior pressure.

7. A flexible intraocular lens according to claim 1, wherein each plate haptic is coupled to the optic by at least one stretchable connection member comprising a hinge.

8. The flexible intraocular lens of claim 1, wherein the optic comprises acrylic.

9. The flexible intraocular lens of claim 1, wherein the optic comprises silicone.

10. The flexible intraocular lens of claim 1, wherein the chassis comprises polyimide.

11. The flexible intraocular lens of claim 1, wherein the pair of plate haptics comprises acrylic.

12. The flexible intraocular lens of claim 1, wherein the pair of plate haptics and the optic each comprise acrylic.

* * * * *